United States Patent [19]

Azuma

[11] Patent Number: 5,494,531
[45] Date of Patent: Feb. 27, 1996

[54] METHOD AND APPARATUS FOR CLEANING MEDICAL INSTRUMENTS

[75] Inventor: Masatoshi Azuma, Nagaoka, Japan

[73] Assignee: Nippon Seiki K.K., Kiigata, Japan

[21] Appl. No.: 305,964

[22] Filed: Sep. 15, 1994

[30] Foreign Application Priority Data

Sep. 30, 1993 [JP] Japan ..................... 5-269822

[51] Int. Cl.$^6$ ...................................... B08B 3/10
[52] U.S. Cl. .................... 134/25.4; 134/26; 134/76; 134/88; 134/105; 134/102.3
[58] Field of Search ................... 134/25.1, 25.4, 134/26, 78, 88, 76, 105, 85, 102.3

[56] References Cited

U.S. PATENT DOCUMENTS

| | | | |
|---|---|---|---|
| 3,869,313 | 3/1975 | Jones et al. | 134/76 |
| 3,937,236 | 2/1976 | Runnells . | |
| 4,710,233 | 12/1987 | Hohmann et al. . | |
| 4,886,082 | 12/1989 | Kato et al. | 134/76 |
| 4,974,619 | 12/1990 | Yu | 134/76 |
| 5,331,987 | 7/1994 | Hayashi et al. | 134/200 |
| 5,361,789 | 11/1994 | Yoshida et al. | 134/76 |

FOREIGN PATENT DOCUMENTS

3934928A1 10/1989 Germany .
56-115680 9/1981 Japan .

*Primary Examiner*—Frankie L. Stinson
*Attorney, Agent, or Firm*—Lowe, Price, LeBlanc & Becker

[57] ABSTRACT

The present invention provides a medical instrument cleaning method and apparatus suitable for thoroughly cleaning medical instruments, particularly instruments used in dental treatment and with strongly adhesive deposits such as cement and the like.

The instrument cleaning process according to the present invention comprising a boiling step of boiling instruments with deposits thereon in a boiling vessel, allowing water to soak into the deposits, a drying step of drying the boiled instruments with hot air in a drying vessel to dry the water-soaked deposits, and a washing step of washing the dried instruments in a washing vessel to remove the dried deposits.

Thus, the instruments with deposits thereon are boiled in the boiling step, in which water soaks into the deposits, then the boiled instruments are dried in the drying step, whereby the water soaked into the deposits is evaporated to weaker the adhesive force of the deposits, and subsequently the dried instruments are washed in the washing step, whereby the deposits which have been made less adhesive are removed from the instruments. In this way the instruments with deposits can be cleaned to a satisfactory extent.

13 Claims, 8 Drawing Sheets

METHOD AND APPARATUS FOR CLEANING MEDICAL INSTRUMENTS

BACKGROUND OF THE INVENTION

1. Field of the Invention

The present invention relates to a method and apparatus for medical instruments and more particularly a cleaning method and apparatus for removing deposits on metallic instruments used in dental treatment.

2. Description of the Prior Art

Heretofore, in dental treatment, there have been used various metallic instruments, including stopper, probe, excavator and pincette, for applying a medicine to an effected part of a patient, grinding a tooth, filling a tooth with a temporary sealant, or fixing a tooth crown through an adhesive. Since the materials which have been used in the dental treatment are deposited on those instruments, the instruments are washed after use to remove such deposits and keep the instruments in good hygienic condition.

As the aforesaid temporary sealant or adhesive there usually is employed cement which has a strong adhesive force. When such a highly adherent material is deposited on a medical instruments it is removed by using a dedicated cleaning apparatus.

According to the said cleaning apparatus, medical instruments which have been used in medical treatments and with deposits thereon can be washed together, and as this type of a cleaning apparatus there is known an ultrasonic washing apparatus wherein a washing basket containing medical instruments is immersed in a washing vessel containing a washing solution and ultrasonic waves are fed by turning a switch ON to effect cleaning automatically (see, for example, U.S. Pat. No. 4,710,233, U.S. Pat. No. 3,937,236 and U.S. Pat. No. DES. 3,934,928).

Also known is an ultrasonic washing apparatus comprising a plurality of vessels and which automatically performs not only washing of medical instruments but also rinsing and drying of the washed instruments (see, for example, Japanese Patent Laid Open No.115680/81). According to this known apparatus, a rinsing vessel for rinsing medical instruments after washing and a drying vessel for drying the rinsed instruments, in addition to a washing vessel for washing medical instruments using ultrasonic waves, are arranged side by side in a row within the same apparatus, and medical instruments contained in a washing basket are conveyed to those vessels successively by means of conveyance mechanism.

However, such conventional ultrasonic washing apparatus are generally low in their washing capacity, so with ultrasonic washing alone it is impossible to thoroughly wash off deposits having a strong adhesive force, and deposits will remain on the washed medical instruments thus requiring a manual operation for removing them which operation is troublesome. The latter ultrasonic washing apparatus comprising plural vessels also involves the problem that the size of the apparatus increases with increase of the floor space, because plural vessels are arranged side by side in a row within the same apparatus.

Besides, in the latter ultrasonic washing apparatus, since the ultrasonic washing vessel and the rinsing vessel each require a water supply pipe, a water discharge pipe and an overflow pipe for the prevention of water overflow, the piping becomes complicated and the piping space expands.

Further, when the operations for maintenance and for mounting are also taken into account, a wide space is required. This point is also a cause of the increase in the size of the apparatus.

SUMMARY OF THE INVENTION

The present invention has been accomplished in view of the abovementioned problems, and it is the first object of the invention to provide a method and apparatus capable of cleaning medical instruments with deposits thereon to a satisfactory extent. It is the second object of the invention to provide a medical instrument cleaning apparatus which permits the operation for maintenance and that for mounting to be done in a simple manner.

According to the present invention, in order to achieve the first object mentioned above, there are provided a boiling step of allowing water to soak into a deposit on a medical instrument, using a boiling vessel for immersing and boiling the instrument in liquid, the boiling vessel having a heating means, a drying step of drying the water-soaked deposit, using a drying vessel provided with a hot air supply means for supplying hot air to the thus-boiled instrument to dry it, and a washing step of removing the dried deposit, using a washing vessel for immersing and washing the thus-dried instrument in liquid.

Thus, the instrument with the deposit thereon is boiled in the boiling vessel which carries out the boiling step, allowing water to soak into the deposit, then is subjected to a drying treatment in the drying vessel which carries out the drying step, allowing the soaked water to evaporate, thereby causing the adhesive force of the deposit to become weaker, then the dried instrument is subjected to a washing treatment in the washing vessel which carries out the washing step, whereby the deposit with weakened adhesive force is removed from the instrument. In this way, the instrument with deposit can be cleaned to a satisfactory extent.

According to the present invention, in order to achieve the second object mentioned above the drying vessel is mounted on the boiling vessel or on the washing vessel, the rinsing vessel is mounted on the washing vessel or on the boiling vessel, a drain portion is formed in the bottom of the rinsing vessel to discharge the inside water to the exterior of the vessel at all times, an overflow portion is provided in the upper portion of the washing vessel or the boiling vessel located under the rinsing vessel to conduct overflowing water to the exterior so as to maintain the water level in the vessel at a predetermined level, and a confluence portion for joining the overflow water from the overflow portion and the water discharged from the drain portion and discharging the joined streams is connected to the overflow portion.

Thus, since the drying vessel or the rinsing vessel is mounted on the boiling vessel or on the washing vessel, it is possible to reduce the size of the apparatus. Moreover, since the water discharged from the rinsing vessel and the overflowing water from the washing vessel or the boiling vessel are discharged together in the confluence portion contiguous to the overflow portion, it is not necessary to provide a drain pipe exclusive for the rinsing vessel, whereby the reduction of size can be realized and the operation for maintenance and that for mounting can be done to a satisfactory extent.

DETAILED DESCRIPTION OF THE PREFERRED EMBODIMENTS

Figure 6:
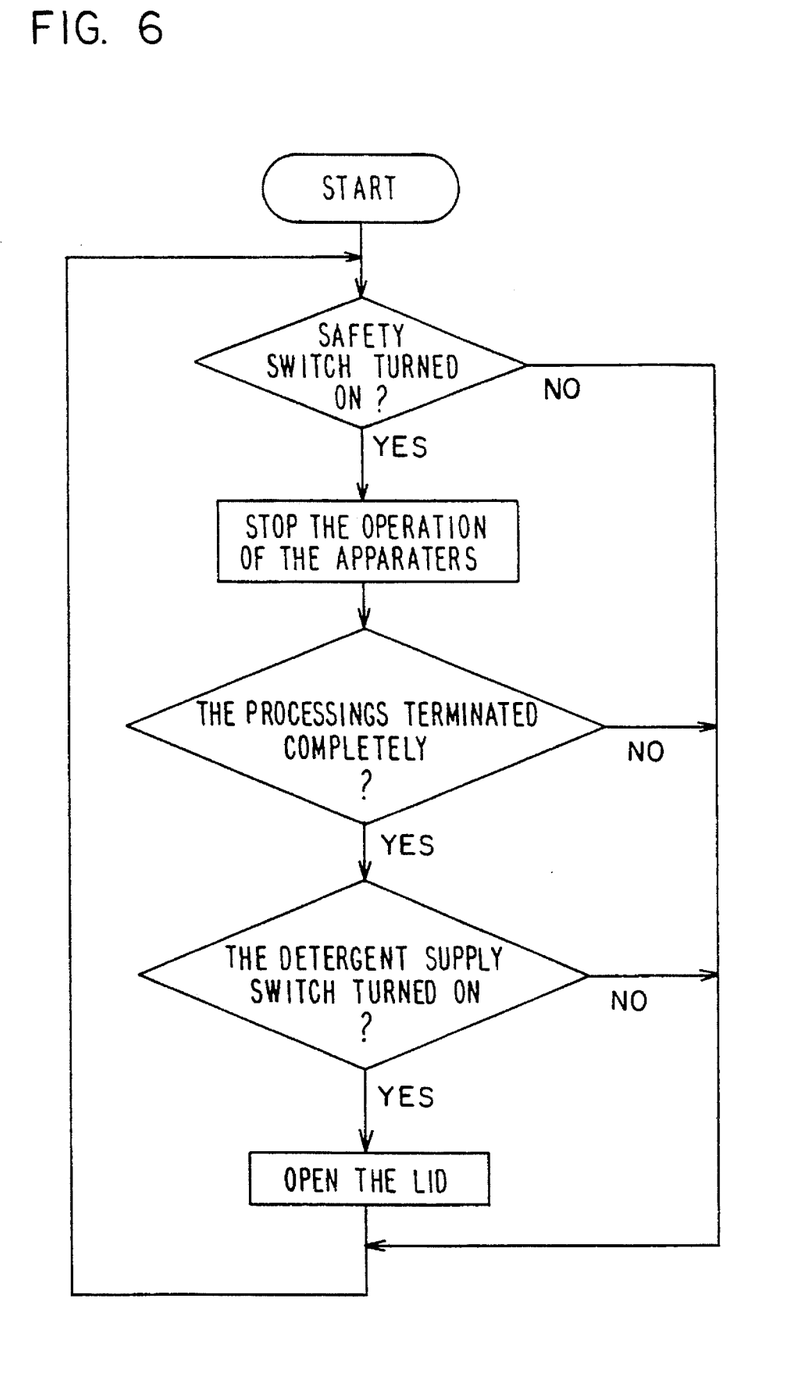
FIG. 6 is a flowchart explaining the processing of the control section executed when a detergent is to be fed.
Figure 7:
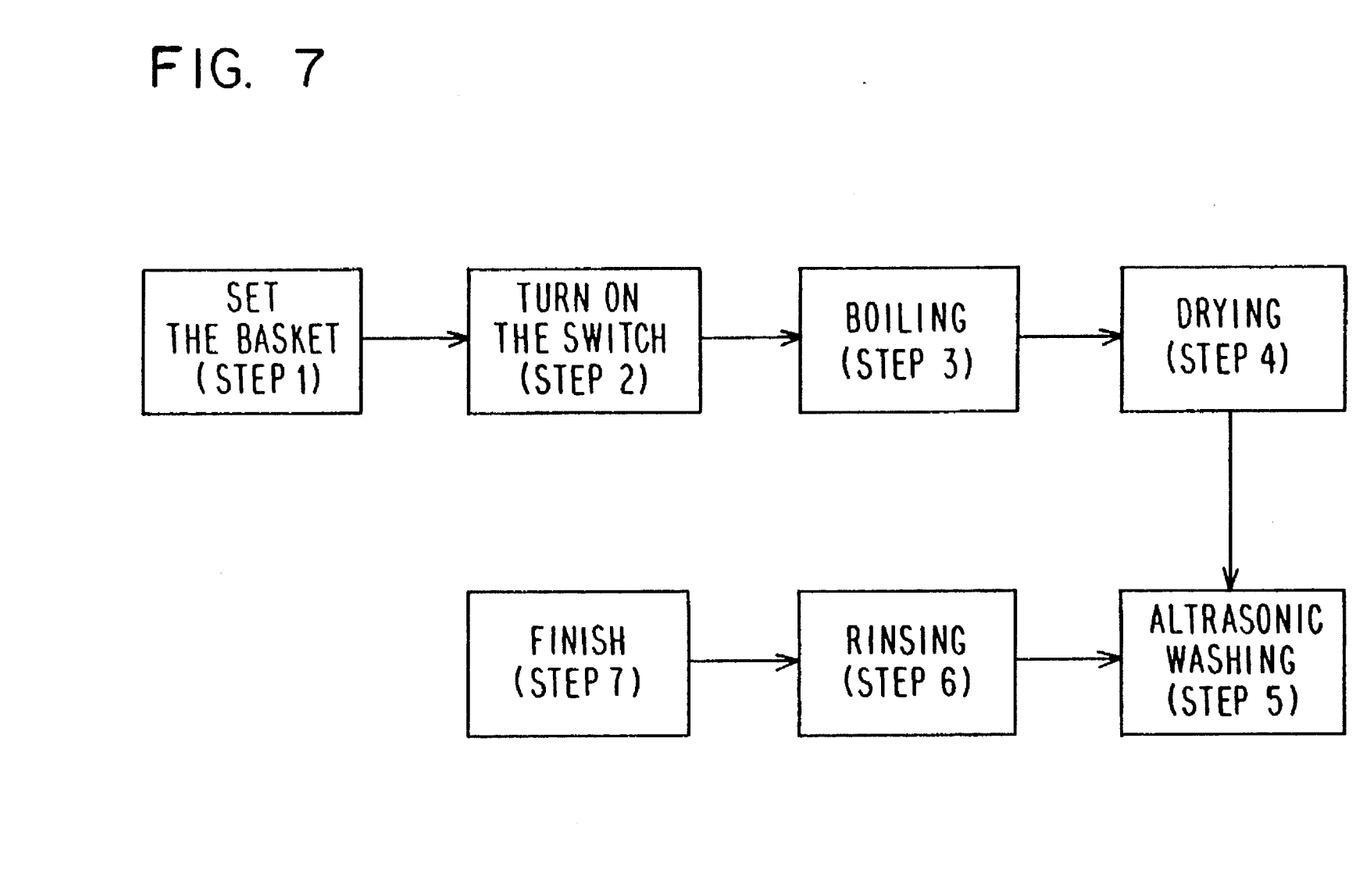
FIG. 7 is a block diagram explaining the operation of the cleaning apparatus and a cleaning process executed thereby.
Figure 8:
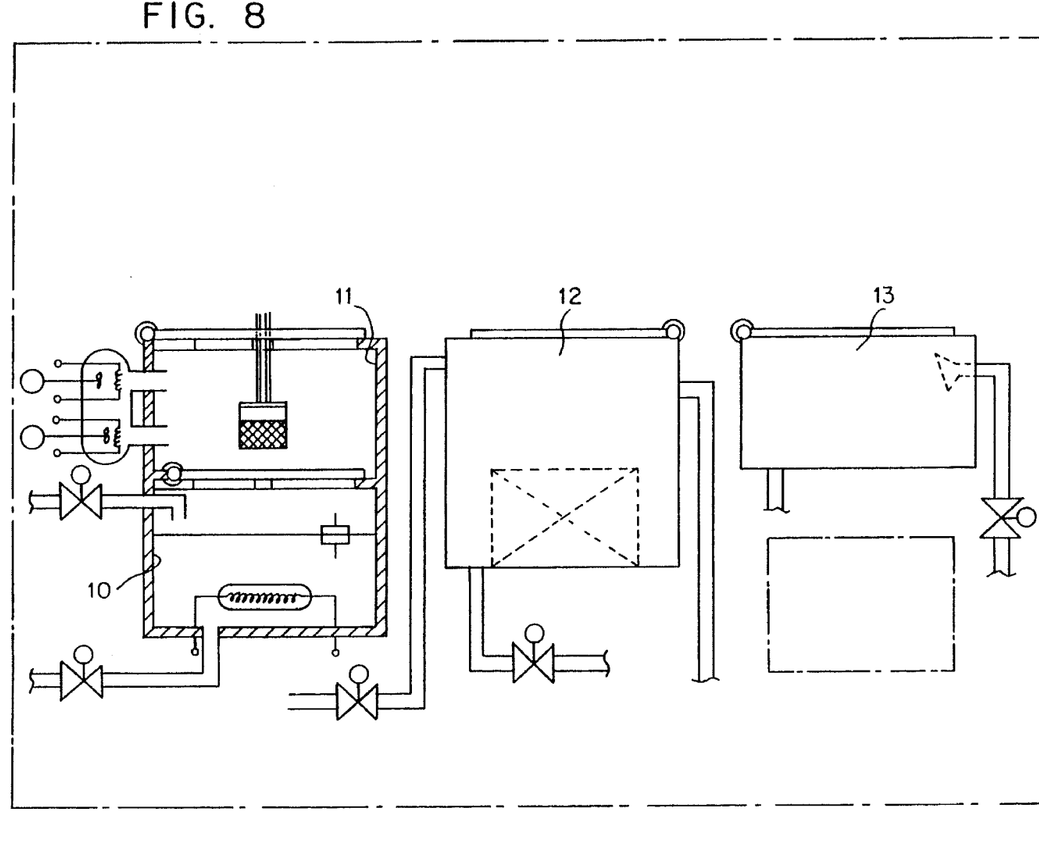
FIG. 8 is a schematic construction diagram explaining an internal structure of a cleaning apparatus according to another embodiment of the present invention.

Apparatus and methods for cleaning medical instruments according to embodiments of the present invention will be described hereinunder with reference to the accompanying drawings, in which FIGS. 1 to 7 illustrate an embodiment of the invention and FIG. 8 illustrates another embodiment of the invention.

Figure 1:
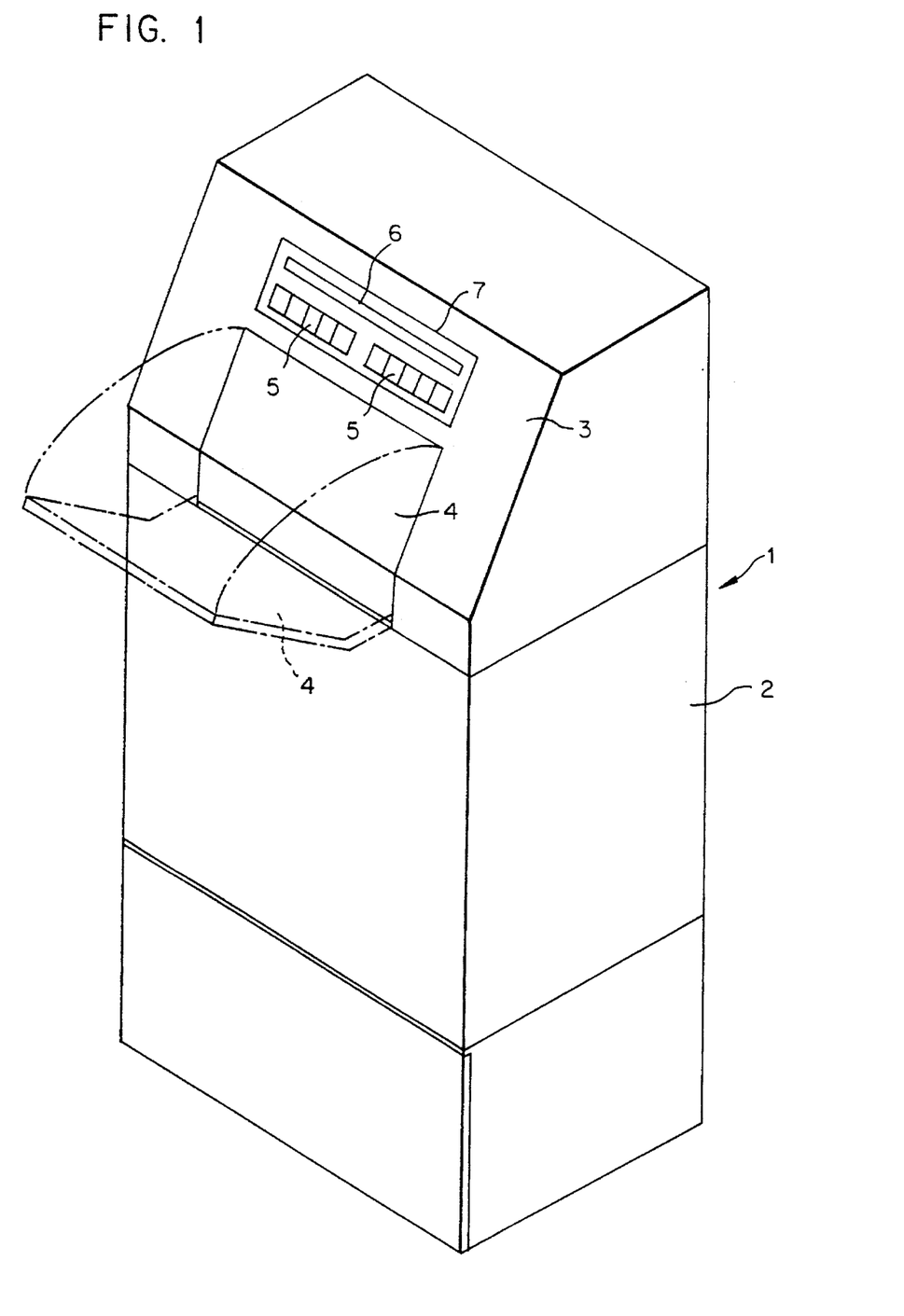
FIG. 1 is a perspective view showing an appearance of a cleaning apparatus according to an embodiment of the present invention.

In FIG. 1, a cleaning apparatus 1 has an outer case 2 which is in the shape of a rectangular parallel-piped and which has a slant portion 3. In the slant portion 3 are provided an outer door 4 capable of being opened and closed and an operation panel 7, the operation panel 7 comprising a plurality of operating switches 5 and an operating state display 6.

Figure 2:
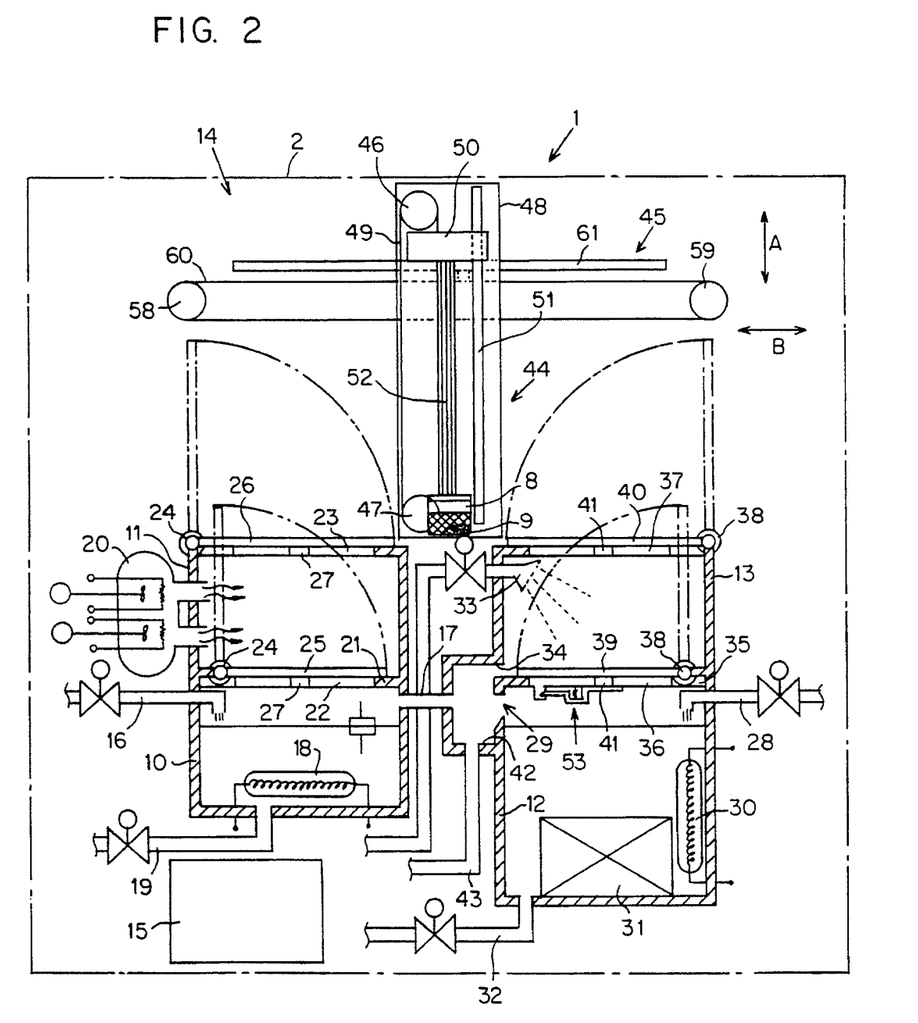
FIG. 2 is a schematic construction diagram explaining an internal structure of the cleaning apparatus illustrated in FIG. 1.

In FIG. 2, the numeral 8 denotes a washing basket containing instruments 9 together on which has been deposited cement, medicine or the like (not shown) in a medical treatment; the numeral 10 denotes a boiling vessel formed of stainless steel for boiling the instruments 9; numeral 11 denotes a drying vessel for drying the instruments 9, the drying vessel 11 being formed of the same material as that of the boiling vessel 10; numeral 12 denotes a washing vessel for washing the instruments 9 using ultrasonic waves, the washing vessel 12 being formed of the same material as that of the boiling vessel 10; numeral 13 denotes a rinsing vessel for rinsing the instruments 9, the rinsing vessel being formed of the same material as that of the boiling vessel 10; numeral 14 denotes a conveyance means for conveying the instruments 9 contained in the washing basket 8 into each of the boiling vessel 10, drying vessel 11, washing vessel 12 and rinsing vessel 13; and numeral 15 denotes a control section comprising a circuit unit for controlling the components of the cleaning apparatus 1 including boiling vessel 10, drying vessel 11, washing vessel 12, rinsing vessel 13 and conveyance means 14. The washing basket 8 is carried manually into the interior of the cleaning apparatus 1 through the outer door 4 formed in the outer case 2 shown in FIG. 1.

The boiling vessel 10 is provided with a liquid supply pipe 60 for supplying liquid, e.g. tap water, into the vessel, an overflow pipe 17 for discharging the water in the vessel to the exterior when the water level in the vessel exceeds a predetermined level, a heating means 18 constituted by an electric heater for heating the water fed into the vessel, and a drain pipe 19 for discharging water which has become unnecessary to the exterior of the vessel. Water is stored into the vessel through the liquid supply pipe 16 and the stored water is heated by the heating means 18 in a soaked state of the washing basket 8 into the stored water to boil the instruments 9. After this boiling treatment for the instruments 9, the stored water can be discharged to the exterior of the vessel through the drain pipe 19.

The drying vessel 11 has a hot air supply means 20 for supplying hot air into the vessel. The hot air supply means 20 functions to apply hot to the instruments 9 through the washing basket 8 which has been introduced into the drying vessel, thereby drying the instruments rapidly.

In this case, the veiling vessel 10 into which water is supplied through the liquid supply pipe 16 and stored for boiling, and the drying vessel 11 which requires neither the supply of water nor the storage of water, are mounted in a stacked fashion such that the drying vessel 11 is located up and the boiling vessel 10 down through a partition wall 21. The washing basket 8 can be introduced into both vessels 10 and 11 through an opening 22 formed in the partition wall 21 and through an opening 23 formed in the top wall portion of the drying vessel 11. Attached to the boiling vessel 10 and drying vessel 11 are lids 25 and 26, respectively, which are driven by motors 24 so as to open and close the openings 22 and 23 automatically. Further, a cutout portion 27 for insertion therein of a later-described arm of the conveyance means 14 is formed in each of the openings 22 and 23. In a closed state of the opening 22, the lid 25 constitutes a part of the bottom wall of the drying vessel 11.

The washing vessel 12 is provided with a liquid supply pipe 28 for supplying liquid, e.g. tap water, into the vessel, an overflow portion 29 for discharging water stored in vessel to the exterior when the inside water level exceeds a predetermined level, an electric heater 30 for heating the water supplied and stored in the vessel, an ultrasonic oscillator 31 for radiating ultrasonic waves to the water stored in the vessel, and a drain pipe 32 for discharging water which has become unnecessary to the exterior of the vessel. A detergent is manually fed into the water stored in the vessel and the stored water is heated by the electric heater 30 to make the stored water into a warm, aqueous detergent solution. Into this detergent solution is then immersed the washing basket 8, and in this state ultrasonic waves are radiated into the solution to effect ultrasonic washing for the instruments 9. After this washing treatment, the detergent solution can be discharged to the exterior of the vessel through the drain pipe 32.

The rinsing vessel 13 is provided with a rinsing water supply means 33 for the supply of rinsing water into the vessel and a drain port 34 formed in the bottom portion of the vessel for discharging rinsing water at all times. When the washing basket 8 is introduced into the rinsing vessel 13, rinsing water is applied to the instruments 9 through the rinsing water supply means 33 to remove residue, if any, of the detergent solution or deposit on the instruments 9 which have gone through the ultrasonic washing in the washing vessel 12.

In this case, the washing vessel 12 into which water is fed through the liquid supply pipe 28 and is stored to effect ultrasonic washing for the instruments 9, and the rinsing vessel 13 into which water is fed through the rinsing water supply means 33 and which does not require the storage of water, are mounted in a stacked fashion such that the rinsing vessel 13 is located up and the washing vessel 12 down through a partition wall 35. The washing basket 8 can be introduced into the vessel 12 and 13 through an opening 36 formed in the partition wall 35 and through an opening 37 formed in the top wall portion of the rinsing vessel 13. Mounted to the washing vessel 12 and the rinsing vessel 13 are lids 39 and 40, respectively, which are driven by motors 3B so as to open and close the openings 36 and 37 automatically. In each of the openings 36 and 37 is provided a cutout portion 41 for insertion therein of an arm of the conveyance means 14 which arm will be described rater. With the opening 36 closed, the lid 39 constitutes a part of the bottom wall of the rinsing vessel 13. Outside the overflow portion 29 of the washing vessel 12 is formed a confluence portion 42 in an integrally extended fashion from the ultrasonic washing vessel 12 and the rinsing vessel 13, the confluence portion 42 joining all of the water discharged from the overflow portion 29, the water discharged from the drain port 34 formed in the rinsing vessel 13 and the water discharged from the overflow pipe 17 connected to the boiling vessel 10. The confluence portion 42 is for collecting the overflow water from each of the washing vessel 12 and boiling vessel 10 and the water discharged from the rinsing vessel 13 and discharging the joined stream to the exterior through the drain pipe 43.

The conveyance means 14 comprises a vertically moving portion 44 for moving the washing basket 8 containing the instruments 9 in the vertical direction (arrow A direction) in accordance with the positions of the stacked vessels 10, 11 and 12, 13 and a laterally moving portion 45 for moving the vertically moving member 44 which holds the washing basket 8 in the lateral direction (arrow B direction).

Figure 3:
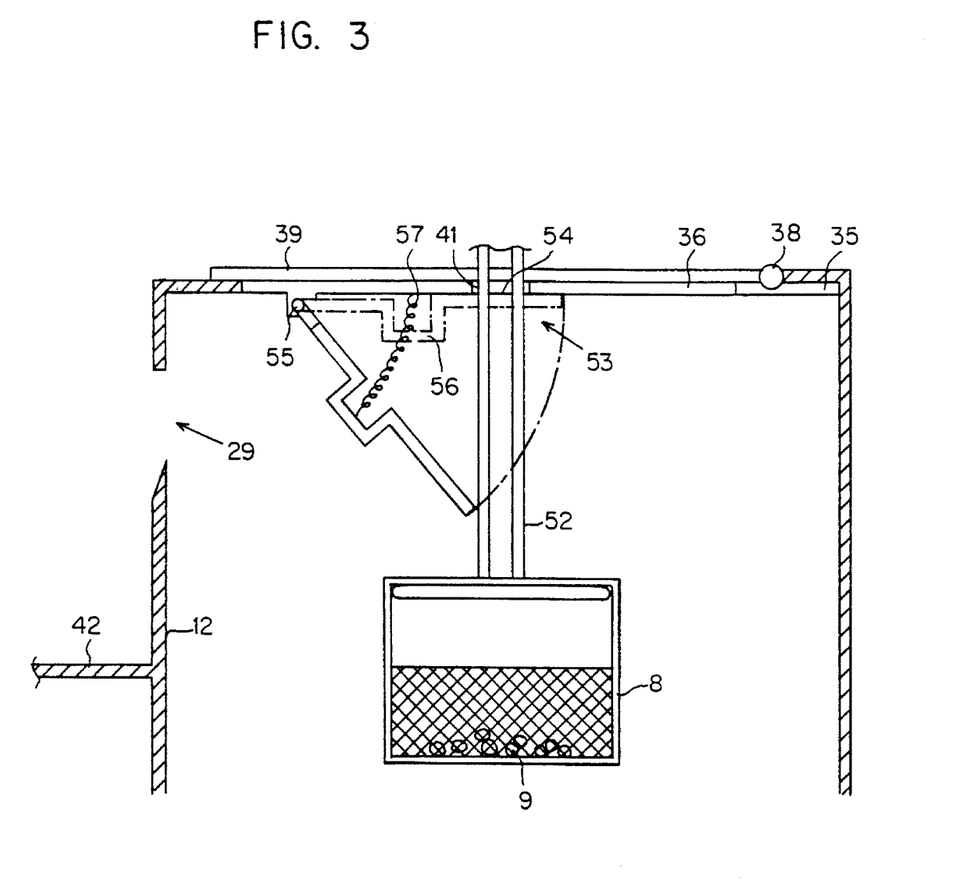
FIG. 3 is a sectional view of a principal portion of FIG. 2.
Figure 4:
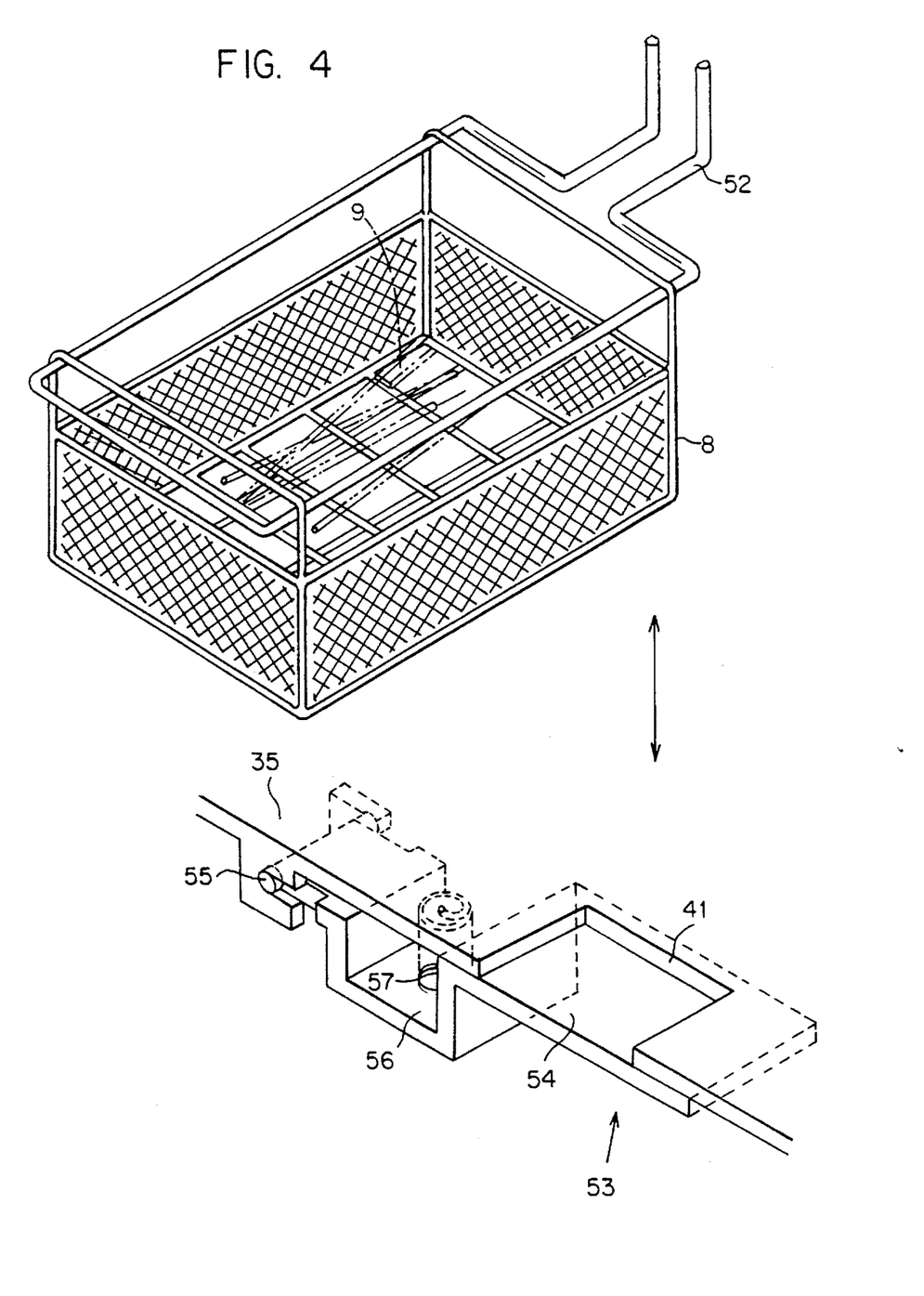
FIG. 4 is a perspective view showing a detailed portion of FIG. 3 together with a washing basket.

The vertically moving portion 44 is constructed as follows. A driving pulley 46 which is driven by a motor (not shown) or the like and a driven pulley 47 are disposed vertically on a movable base 48, an endless belt 49 is stretched between both pulleys 46 and 47, a response member 50 is secured to the endless belt 49 so as to be movable vertically in the direction of arrow A along a guide 51 provided on the movable base 48, an L-shaped arm 52 is fixed to the response member 50, and the washing basket 8 is held in a suspended state by the lower end portion of the arm 52. When the washing basket 8 is to be conveyed to each of the vessels 10, 11, 12 and 13, the arm 52 of the vertically moving portion 44 is partially fitted in the cutout portion 27 in the opening 22 or 23 or the cutout portion 41 in the opening 36 or 37, whereby the washing basket 8 is conveyed to the interior of the vessel 10, 11, 12 or 13. To the partition wall 35 is mounted a lid member 53 for closing the cutout portion 41. As shown in FIGS. 3 and 4, the lid member 53 is provided with a flat portion 54 for closing the cutout portion 41, a pivot portion 55 which provides a pivotable support relative to the partition wall 35, and a concave portion 56 formed between the pivot portion 55 and the flat portion 54. Both ends of a spring 57 are anchored to the concave portion 56 and the partition wall 35, respectively. When the washing basket 8 is to be conveyed into the washing vessel 12, the arm 52 moves down and comes into abutment with the lid member 53, so that the lid member 53 pivotally moves downward to open the cutout portion 41, thereby permitting the insertion of the arm 52 into the cutout portion 41, whereby the washing basket 8 can be received within the washing vessel 12. When the washing basket 8 is not to be introduced into the washing vessel 12, the cutout portion 41 is closed to prevent the entry of rinsing water from the rinsing vessel 13 into the washing vessel 12.

The laterally moving portion 45 is constructed as follows. Substantially similarly to the vertically moving portion 44 described above, a pair of driving pulley 58 which is driven by a motor (not shown) or the like and driven pulley 59 are mounted to a machine frame (not shown) in left and right positions, respectively, an endless belt 60 is stretched between the pulleys 58 and 59, and the movable base 48 of the vertically moving portion 44 is secured to the endless belt 60 so as to be movable in the direction of arrow B along a guide rail 61 mounted to the machine frame referred to above.

Figure 5:
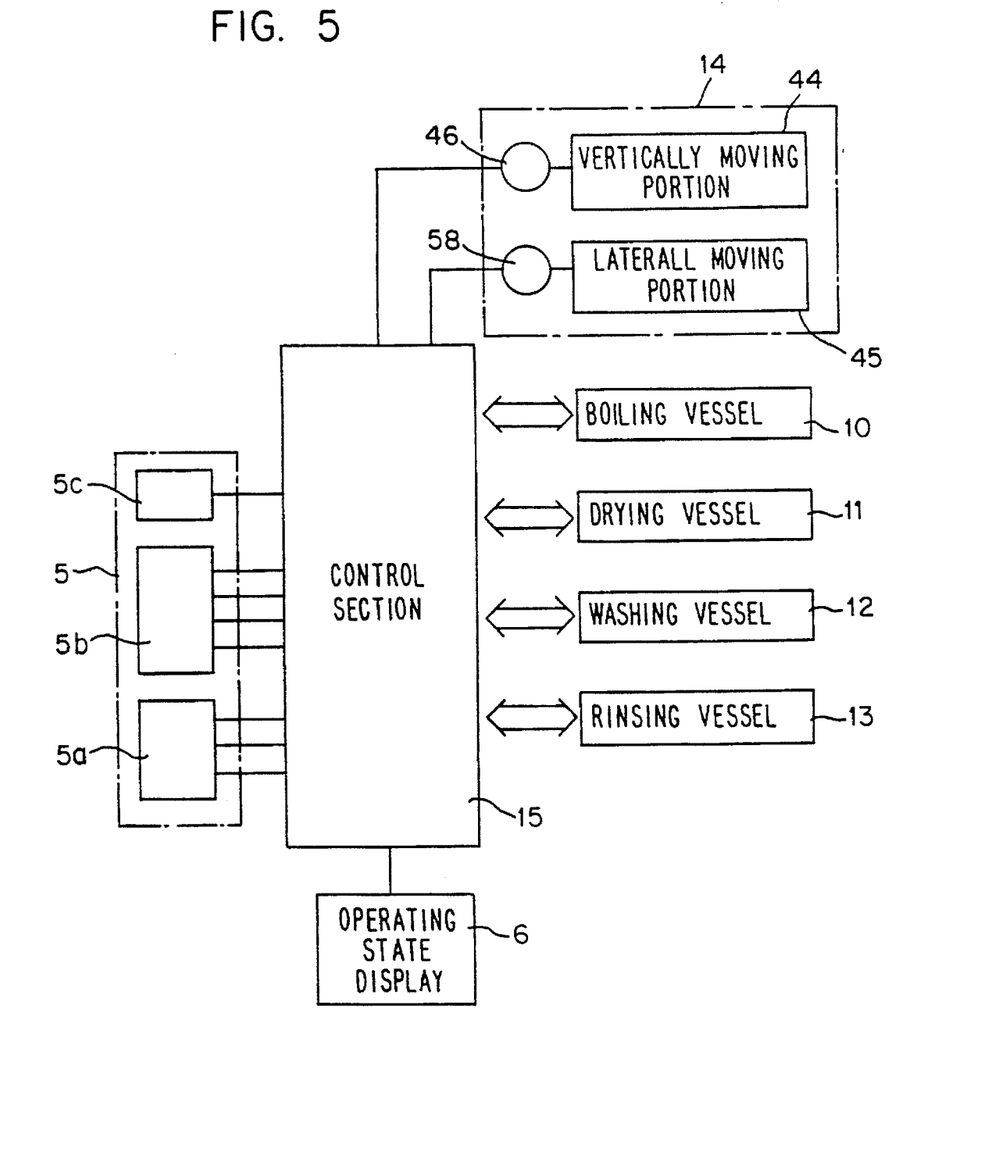
FIG. 5 is a circuit block diagram for explaining a control section.

As shown in FIG. 5, upon turning ON of plural operating switches 5 provided as setting switches on the operation panel 7 (see FIG. 1), the control section 15 controls the operation of the conveyance means 14, the state and processing conditions such as processing time of each of the vessels 10, 11, 12 and 13, and the operation of the operating state display 6. As to the state of each of those vessels, the control section 15 controls opening and closing of the lids 25, 26, 39 and 40, the supply and discharge of water in accordance with an output signal from a level sensor (not shown) in the boiling vessel 10, setting of the water temperature for the heating means 18 in accordance with an output signal from a temperature sensor (not shown), the supply of hot air for the hot air supply means 20 in the drying vessel 1, the supply and discharge of water in accordance with an output signal from a level sensor (not shown) in the washing vessel 12, setting of the water temperature for the electric heater 30 in accordance with an output signal from a temperature sensor (not shown), the supply of ultrasonic waves for the ultrasonic oscillator 31, and the supply of rinsing water for the rinsing water supply means 33 in the rinsing vessel 13. The operating switches 5 serving as setting switches include a manual mode selection switch 5a for manual operation to execute processings in the vessels 10, 11, 12 and 13, an automatic mode selection switch 5b for causing various processings in those vessels to be carried out in a series of automatic modes which have been predetermined in accordance with the degree of stain, etc. of the instruments 9, and a detergent supply switch 5c for permitting the supply of a detergent into the washing vessel 12. The control section 15 causes the cleaning operation for the instruments 9 to be executed in accordance with the mode selected by the operating switch 5a or 5b and causes the lid 39 of the washing vessel 12 to be opened to permit the supply of a detergent into the vessel. In the cleaning apparatus of this embodiment, moreover, the outer door 4 is provided with a safety switch (not shown) for detecting that the outer door is open. When this safety switch has detected that the outer door 4 is open, the control section 15 makes control to stop the operation of the conveyance mechanism 14 and that of the vessels 10, 11, 12 and 13, thereby ensuring safety of the operator.

The control section 15 is programmed in such a manner that when a detergent is to be fed into the washing vessel, the lid 39 of the ultrasonic washing vessel 12 is not opened even with the detergent supply switch 5c turned ON if the operation of the apparatus is stopped in an open condition of the outer door 4 detected by the safety switch and if the processings in the vessels 10, 11, 12 and 13 are not terminated completely, as shown in FIG. 6. Thus, the safety at the time of supply of a detergent is also taken into consideration so that the detergent cannot be fed into the washing vessel even when, for example, the operator becomes aware of having forgotten to put the detergent into the vessel during execution of the washing step and even if he tries to put the detergent into the vessel forcibly.

Now, the processing steps and operations in this embodiment will be described below on the basis of FIG. 7 and also with reference to FIGS.1 and 2 while referring as an example to the case where one mode switch in the automatic mode selection switch 5b out of the operating switches 5 has been turned ON.

First, the outer door 4 is opened, the detergent supply switch 5c is turned ON, allowing the detergent to be fed into the washing vessel 12, and the washing basket 8 containing the instruments 9 is suspended from the arm 52 of the conveyance means 14 which is in a reset state as shown in FIG. 2 (step 1).

Next, the operating switch 5b is depressed selectively (step 2), whereupon the lids 26 and 25 open successively in this order and the conveyance means 14 conveys the washing basket 8 into the boiling vessel 10. Then, the lid 25 closes, followed by closing of the lid 26, and boiling of the instruments 9 is performed (step 3). In this boiling step, deposits such as cement and medicines on the instruments 9 are dissolved and water soaks into the deposits. When step 3 is over, the lid 26 opens, followed by opening of the lid 25, and the conveyance means 14 conveys the washing basket 8 to the original position shown in FIG. 2.

Subsequently, only the lid 25 closes, and the conveyance means 14 carries the washing basket 8 into the drying vessel 11, then the lid 26 is closed and the instruments 9 are dried rapidly by the supply of hot air (step 4). At this time, the water which has soaked into the deposits in step 3 expands and evaporates, but since the deposits per se undergo little change, the deposits will be destroyed themselves by the evaporating action of water, or their adhesive force will be deteriorated because the water once soaked in the interface between the deposits and the instruments 9 escape from the interface. When step 4 is over, the lid 26 is opened and the conveyance means 14 carries the washing basket 8 to the original position shown in FIG. 2, followed by closing of the lid 26.

Next, the lid 40 opens, followed by opening of the lid 39, and the conveyance means 14 carries the washing basket 8 into the washing vessel 12. Then, the lids 39 and 40 close successively in this order and ultrasonic washing is performed for the instruments 9 (step 5). In this washing step, the deposits which were rendered less adhesive in step 4 are removed from the instruments 9 by the ultrasonic washing in the detergent solution. When step 5 is over, the lid 40 opens, followed by opening of the lid 39, and the conveyance means 14 carries the washing basket 8 to the original position shown in FIG. 2.

Next, only the lid 39 closes and the conveyance means 14 carries the washing basket 8 into the rinsing vessel 13. Subsequently, the lid 40 closes and rinsing of the instruments 9 is performed (step 6). In this rinsing step, residual deposits of medicines, etc. on the instruments 9 after step 5 are removed by rinsing water. When step 6 is over, the lid 40 opens and the conveyance means 14 carries the washing basket 8 to the original position shown in FIG. 2, followed by closing of the lid 40. Now, a series of processing steps are over, that is, a finishing step is completed (step 7).

According to this embodiment covering both cleaning method and apparatus 1, as set forth above, there are provided a boiling step (step 3) for allowing water to soak into deposits on the instruments 9, using the boiling vessel 10 provided with the heating means 18 for boiling the instruments 9 in an immersed state in liquid, a drying step (step 4) for evaporating the water soaked into the deposits to weaken the adhesive force of the deposits, using the drying vessel 11 provided with the hot air supply means 20 for supplying hot air to the instruments 9 after boiling in the boiling vessel 10 to dry the instruments, a washing step (step 5) for removing from the instruments 9 the deposits which have been rendered less adhesive in step 4, using the washing vessel 12 provided with the ultrasonic oscillator 31 for ultrasonic-washing the instruments 9 in an immersed state in liquid after drying in the drying vessel 11, and a rinsing step (step 6) for removing residual deposits on the instruments 9 after ultrasonic washing, using the rinsing vessel 13 in which rinsing of the instruments 9 is performed by pouring rinsing water to the instruments after washing in the washing vessel 12. Thus, the instruments 9 with deposits thereon are boiled in the boiling vessel in the boiling step (step 3), allowing water to soak into the deposits, then are dried in the drying vessel in the drying step (step 4), allowing the water soaked in the deposits to evaporate to weaker the adhesive force of the deposits, then are washed in the washing vessel in the washing step (step 5), whereby the deposits weakened in their adhesive force are removed from the instruments, further, the instruments 9 after washing are rinsed in the rinsing vessel 13 in the rinsing step (step 6), whereby residual detergent solution or deposits, if any, are removed. In this way the instruments with deposits can be cleaned to a satisfactory extent.

In the cleaning apparatus 1 of this embodiment constructed as above, the drying vessel 11 and the rinsing vessel 13 are formed on the underlying boiling vessel 10 and ultrasonic washing vessel 12, respectively, so when the apparatus is constituted by arranging the vessels 10, 11, 12 and 13, it is possible to enhance the space efficiency and attain the reduction in size of the apparatus.

In the cleaning apparatus 1 of this embodiment, moreover, the confluence portion 42 is provided outside the overflow portion 29 of the washing vessel 12 to join the water discharged from the said overflow portion, the water discharged from the drain port 34 formed in the rinsing vessel 13 and the water from the overflow pipe 17 connected to the boiling vessel 10, whereby the overflowing water from each of the washing vessel 12 and the boiling vessel 10, as well as the water discharged from the rinsing vessel 13, can be discharged together to the exterior. Therefore, it is not necessary to provide the rinsing vessel 13 and the boiling vessel 10 with dedicated drain pipe and overflow pipe, respectively, whereby not only the reduction in size of the apparatus can be attained but also it is possible to simplify the piping and perform the operation for maintenance and that for mounting efficiently.

Although in the above embodiment the drying vessel 11 and the rinsing vessel 13 are formed on the boiling vessel 10 and the washing vessel 12, respectively, there also may be adopted such a construction as illustrated as another embodiment in FIG. 8 in which the drying vessel 11 is formed on the boiling vessel 10, while the ultrasonic washing vessel 12 and the rinsing vessel 13 are not stacked.

What is claimed is:

1. A medical instrument cleaning method comprising:
   a boiling step of boiling medical instruments with deposits thereon, thereby allowing water to soak into said deposits;
   a drying step of supplying hot air to said instruments which have been treated in said boiling step, to dry the water-soaked deposits; and
   a washing step of washing said instruments which have been treated in said drying step, to remove the dried deposits from the instruments.

2. A medical instrument cleaning method comprising:
   a boiling step of boiling medical instruments with deposits thereon, thereby allowing water to soak into said deposits;
   a drying step of supplying hot air to said instruments which have been treated in said boiling step, to dry the water-soaked deposits;

a washing step of washing said instruments which have been treated in said drying step, to remove the dried deposits from the instruments; and a rinsing step of rinsing said instruments which have been treated in said washing step.

3. A medical instrument cleaning method according to claim 1, wherein the washing in said washing step is performed using ultrasonic waves.

4. A medical instrument cleaning apparatus comprising:

a boiling vessel provided with a heating means therein for boiling instruments with deposits thereon in an immersed state in liquid;

a drying vessel provided with a hot air supply means for supplying hot air to said instruments which have been boiled in said boiling vessel; and a washing vessel for washing said instruments in an immersed state in liquid after drying in said drying vessel.

5. A medical instrument cleaning apparatus according to any of claim 4, wherein said washing vessel is provided with an ultrasonic oscillator for washing the instruments with ultrasonic waves.

6. A medical instrument cleaning apparatus comprising:

a boiling vessel provided with a heating means therein for boiling instruments with deposits thereon in an immersed state in liquid;

a drying vessel provided with a hot air supply means for supplying hot air to said instruments which have been boiled in said boiling vessel;

a washing vessel for washing said instruments in an immersed state in liquid after drying in said drying vessel; and a conveyance means for conveying said instruments to each of said boiling vessel, said drying vessel and said washing vessel.

7. A medical instrument cleaning apparatus according to claim 6, wherein said drying vessel is located on said boiling vessel.

8. A medical instrument cleaning apparatus according to claim 7, wherein a lid adapted to open and close in accordance with the movement of said instruments by said conveyance means and which lid in a closed state forms the bottom of said drying vessel, is provided on top of at least said boiling vessel.

9. A medical instrument cleaning apparatus comprising:

a boiling vessel provided with a heating means therein for boiling instruments with deposits thereon in an immersed state in liquid;

a drying vessel provided with a hot air supply means for supplying hot air to said instruments which have been boiled in said boiling vessel;

a washing vessel for washing said instruments in an immersed state in liquid after drying in said drying vessel; and a rinsing vessel provided with a rinsing water supply means for supplying rinsing water to said instruments to rinse the instruments.

10. A medical instrument cleaning apparatus comprising:

a boiling vessel provided with a heating means therein for boiling instruments with deposits thereon in an immersed state in liquid;

a drying vessel provided with a hot air supply means for supplying hot air to said instruments which have been boiled in said boiling vessel;

a washing vessel for washing said instruments in an immersed state in liquid after drying in said drying vessel;

a rinsing vessel provided with a rinsing water supply means for supplying rinsing water to said instruments to rinse the instruments; and a conveyance means for conveying said instruments to each of said boiling vessel, said drying vessel, said washing vessel and said rinsing vessel.

11. A medical instrument cleaning apparatus according to claim 10, wherein said drying vessel is located on top of said boiling vessel, and said rinsing vessel is located on top of said washing vessel.

12. A medical instrument cleaning apparatus according to claim 11, wherein lids adapted to open and close in accordance with the movement of said instruments by said conveyance means and which lids in a closed state form the bottoms of said drying vessel and said rinsing vessel, are provided on top of at least said boiling vessel and said washing vessel.

13. A medical instrument cleaning apparatus according to claim 11, wherein a drain portion for discharging rinsing water at all times to the exterior of said rinsing vessel is provided in the rinsing vessel, an overflow portion for maintaining the liquid level in said washing vessel is provided in the upper portion of the washing vessel, and a confluence portion for joining the overflowing liquid from said overflow portion and the water discharged from said rinsing vessel and discharging the joined stream to the exterior is formed outside said washing vessel.

* * * * *